United States Patent [19]

Tustin et al.

[11] Patent Number: 5,719,315
[45] Date of Patent: Feb. 17, 1998

[54] PROCESS FOR THE PREPARATION OF VINYL ACETATE

[75] Inventors: Gerald Charles Tustin; Joseph Robert Zoeller; Leslie Sharon Depew, all of Kingsport, Tenn.

[73] Assignee: Eastman Chemical Company, Kingsport, Tenn.

[21] Appl. No.: 766,258

[22] Filed: Dec. 13, 1996

[51] Int. Cl.$^6$ ................................................ C07C 67/00
[52] U.S. Cl. ................................................ 560/238
[58] Field of Search ................................................ 560/238

[56] References Cited

U.S. PATENT DOCUMENTS 2,422,679  6/1947  Hull et al. ............................ 560/238

FOREIGN PATENT DOCUMENTS 0 348 309  12/1989  European Pat. Off. .

Primary Examiner—Gary Geist
Assistant Examiner—Rosalynd Keys
Attorney, Agent, or Firm—Michael J. Blake; Harry J. Gwinnell

[57] ABSTRACT

This invention pertains to the preparation of vinyl acetate by contacting within a contact zone a mixture of ketene and acetaldehyde with an acid catalyst at about one bar pressure and between about 85° and 200° C. and removing the reaction products from the contact zone.

19 Claims, No Drawings

PROCESS FOR THE PREPARATION OF VINYL ACETATE

The Government of the United States of America has rights in this invention pursuant to Cooperative Agreement No. DE-FC22-95PC93052 awarded by the U.S. Department of Energy.

This invention relates to a process for producing vinyl acetate by reacting ketene and acetaldehyde in a contact zone in the presence of an acid catalyst.

BACKGROUND OF THE INVENTION

Vinyl acetate is an important industrial chemical. Most of the vinyl acetate used industrially is polymerized to poly (vinyl acetate). This important polymer and its derivatives find extensive uses as adhesives, paints and other coatings, films and laminating materials.

Vinyl acetate has been produced commercially by reacting acetylene with acetic acid at 180°–210° C. in a vapor phase process. Although the yields based on acetylene and acetic acid typically exceed 90% for both reactants, the high cost of acetylene, as well as the safety and handling problems associated with its use, make this process disadvantageous when compared to ethylene-based processes.

An example of an ethylene-based vinyl acetate process uses acetaldehyde and acetic anhydride as starting materials. Ethylene is used to produce acetaldehyde by the Wacker oxidation process, and the resulting acetaldehyde is reacted with the acetic anhydride in the presence of an acid catalyst to produce ethylidene diacetate (EDA). The EDA is then heated in the presence of acid catalyst to produce vinyl acetate, acetic acid, acetic anhydride and acetaldehyde. This EDA cracking reaction is disadvantageous for at least two reasons: 1) by-product acetic acid is produced, which then must be converted back to acetic anhydride or otherwise used or disposed of, and 2) unfavorable equilibria exist among EDA, the desired products (vinyl acetate and acetic acid) and the undesired original starting materials (acetaldehyde and acetic anhydride). Thus, the EDA cracking reaction must be performed in the presence of a large excess of acetic anhydride to increase the amount of vinyl acetate and acetic acid produced relative to acetaldehyde. However, even when excess acetic anhydride is added to the EDA cracking reactor, the product distilled from the reactor still contains large amounts of acetaldehyde, acetic anhydride and acetic acid in addition to the desired vinyl acetate. Hence, this process requires multiple distillations and extensive recycling. Because of these problems, coupled with the corrosiveness and safety and handling problems associated with the Wacker process, it is more economical to produce vinyl acetate by the direct reaction of ethylene, acetic acid and oxygen.

Currently, the preferred route to vinyl acetate is the direct reaction of ethylene, acetic acid and oxygen to produce vinyl acetate, water and byproducts. The preferred version of this process uses a heterogeneous catalyst and is performed in the vapor phase at 5–10 bar at 150°–200° C. Because of the explosion hazards associated with this reaction, the reaction must be performed with less than a stoichiometric amount of oxygen; hence, conversions of ethylene, acetic acid and oxygen are typically 10–15%, 15–30% and 60–90% respectively. About 5–10% of the ethylene is converted to carbon dioxide and about 1% is converted to acetaldehyde. The low ethylene and acetic acid conversions per pass require extensive recycling along with a carbon dioxide removal system. Although the capital costs of an ethylene-acetic acid-oxygen-based vinyl acetate plant are high, these capital costs are offset by the generally low costs of ethylene and acetic acid. Thus, a need exists for a process for preparing vinyl acetate having higher conversions per pass and lower yield loss to carbon dioxide than the ethylene-acetic acid-oxygen-based route. The process of the present invention, unlike the ethylene-acetic acid-oxygen-based route, indeed produces vinyl acetate in high conversions per pass and does not produce significant quantities of carbon dioxide.

Other attempts at producing vinyl acetate have also been tried. For example, a number of these attempts seek to prepare vinyl acetate from mixtures of carbon monoxide and hydrogen (synthesis gas) because of the very low cost of raw materials. As initial steps, these schemes convert synthesis gas to methanol or dimethyl ether. In addition, many combinations have been tried in which methyl acetate (produced from methanol and recycled acetic acid) or dimethyl ether are carbonylated to produce acetic anhydride. In some schemes, acetic anhydride is partially hydrogenated to produce EDA and acetic acid. In still other schemes, the methyl acetate or dimethyl ether is carbonylated in the presence of hydrogen to produce EDA and acetic acid in one step. Variations on this approach include reacting methanol or methyl acetate with hydrogen and carbon monoxide to produce acetaldehyde and water or acetaldehyde and acetic acid, respectively; however, the selectivity to acetaldehyde in these reactions is poor. The resulting acetaldehyde is then reacted with the acetic anhydride to produce EDA.

None of these all-synthesis gas routes is economically competitive with the current commercial process based on ethylene, acetic acid and oxygen. Because the production of vinyl acetate by a synthesis gas-based process ultimately involves a cracking reaction of EDA, the process is plagued by most of the same operational difficulties of the above-mentioned EDA process based on ethylene-derived acetaldehyde and acetic anhydride. Further, most of the all-synthesis gas based routes require that two moles of acetic acid be recycled or otherwise used. The methanol hydrocarbonylation route is somewhat advantageous, theoretically, in that the only coproduct, acetic acid, is produced from the EDA cracking step; but, this advantage is offset by the poor selectivity to acetaldehyde, which is characteristic of these reactions.

As noted above, all-synthesis gas based processes based on EDA cracking coproduce acetic acid that must be recycled or otherwise used or disposed of. Thus, a need exists for a process to prepare vinyl acetate that does not have the large acetic acid recycle feature characteristic of processes based on EDA cracking. Because the process of the present invention produces vinyl acetate directly from acetaldehyde and ketene, without significant acetic acid coproduction, the process of the invention does not have a significant acetic acid recycle problem and does not require a large scale acetic anhydride manufacturing step.

The process of the invention has not been described previously. In contrast to the present invention, most of the previous processes that use acetaldehyde as a starting material also use acetic anhydride as a starting material in order to make EDA, which is then cracked to acetic acid and vinyl acetate. U.S. Pat. No. 2,425,389 teaches that the preferred catalysts for cracking EDA to acetic acid and vinyl acetate are aromatic hydrocarbon sulfonic acids and that the cracking reaction should be performed in the presence of at least a three-fold molar excess of acetic anhydride over EDA to drive the equilibrium to acetic acid and vinyl acetate. The process of U.S. Pat. No. 2,425,389 also teaches that acetic anhydride must continuously be added to the mixture to replace that which is depleted.

In *Hydrocarbon Processing* 44 (11), 278 (1965) the process described for continuously producing vinyl acetate from acetaldehyde and acetic anhydride reacts acetaldehyde and acetic anhydride together in one reactor to produce EDA; the EDA is then cracked in a separate reactor tower to produce vinyl acetate and acetic acid, which are removed overhead along with acetaldehyde. A series of distillations are performed to separate and recover vinyl acetate, acetic acid and acetaldehyde. The acetaldehyde is then recycled to the EDA reactor. The process of the present invention, on the other hand, does not require the continuous introduction of acetic anhydride and produces, at most, only trace amounts of acetic acid when performed under the preferred conditions.

Brady, in *The Chemistry of Ketenes, Allenes and Related Compounds*, Part 1, S. Patai (editor), John Wiley and sons, New York, 292 (1980), teaches that ketenes and aldehydes react in the presence of Lewis acids to produce beta-lactones. Thus, Japanese patent application No. 47-25065 teaches that ketene and acetaldehyde react at 5°–15° C. in the presence of the Lewis acid boron trifluoride to produce beta-butyrolactone and compares the activity of this catalyst with those of other Lewis acids such as zinc chloride and iron tetrafluoroborate. Japanese Patent Applications Nos. 49-131718 and 49-134954 teach that silica-alumina catalysts (which possess both Lewis and Bronsted acidity) are also active catalysts for the conversion of ketene and acetaldehyde into beta-butyrolactone at 10°–15° C. Thus, the prior art teaches away from the invention because when ketene and acetaldehyde are reacted in the presence of Lewis acids or the solid acid silica-alumina, which possesses both Lewis and Bronsted acid character, the result is beta-butyrolactone.

It is well known that ketenes can react with enolizable ketones in the presence of Bronsted acids to produce enolic esters at 50°–100° C. as described, for example, in U.S. Pat. No. 2,487,849. Further, Japanese Patent Application No. 48-75510 indicates that the efficiency of the reaction of ketene with enolizable carbonyl compounds using the catalysts system disclosed therein is related to the ease of enolization of the carbonyl compound. In particular, in the presence of the Bronsted acid-based catalyst system of Japanese Patent Application No. 48-75510, ethyl acetoacetate reacts with ketene more readily than does acetone to produce the corresponding enol esters. In addition, March, in *Advanced Organic Chemistry*, 4th Ed., John Wiley and Sons, New York, 585 (1992), teaches that the rate of acid-catalyzed enolization is proportional to the concentration of protonated carbonyl present. In this same reference, on page 250, March shows that it is approximately 1000 times more difficult to protonate an aliphatic aldehyde than it is to protonate an aliphatic ketone with an arene sulfonic acid. Thus, the prior art teaches that it should be very difficult to prepare an enol ester from an aliphatic aldehyde.

U.S. Pat. No. 2,422,679 describes the reaction of ketenes with aldehydes to produce unsaturated carboxylic esters in the presence of a strong Bronsted acid catalyst in a temperature range of zero to 80° C. U.S. Pat. No. 2,422,679 emphasizes that strong acid catalysts, such as sulfuric acid, are preferable to weaker acids such as p-toluenesulfonic acid, which is in accord with the teachings of U.S. Pat. No. 2,487,849, Japanese Patent Application No. 48-75510 and those of March above. Even when sulfuric acid is used as the catalyst, the efficiency of the process of U.S. Pat. No. 2,422,679 is low; and, when about 5.4 moles of acetaldehyde are reacted with 2 moles of ketene (bubbled through the acetaldehyde-sulfuric acid mixture at 15° C.), only about 21% of the ketene is converted to vinyl acetate after the mixture is distilled. (Note that the numbers provided in Example 1 of this patent are consistent with the ketene conversion to vinyl acetate being about 21% rather than the acetaldehyde conversion being 21%; the conversion of acetaldehyde to vinyl acetate calculates to about 8% based on the Example 1 numbers.) The process of the present invention is a definite improvement over the process of U.S. Pat. No. 2,422,679 because higher yields, based on both ketene and acetaldehyde, are obtained in the present invention by using higher temperatures and weaker catalysts under continuous conditions rather than the lower temperatures and stronger catalysts under the batch or semi-batch conditions in U.S. Pat. No. 2,422,679.

European Patent Application 0 348 309 A1 describes a process to convert EDA into vinyl acetate in the presence of a ketene stream and an acid catalyst (preferably sulfuric acid). The ketene in that process reacts with acetic acid produced from the EDA cracking thus producing acetic anhydride; as the acetic anhydride level builds up, a modest increase in the amount of vinyl acetate produced is observed compared to that produced in the absence of ketene. However, in the process of European Patent Application 0 348 309 A1, much of the ketene is wasted and the vinyl acetate production decreases as EDA is depleted. Further, the EDA used in the process of European Patent Application 0 348 309 A1 must be produced in a separate step before the reaction can proceed. The process of the current invention is much more efficient than that of European Patent Application 0 348 309 A1 because a separate EDA production step is not required; in the present invention, both ketene and acetaldehyde are fed to the reactor together, and ketene use is much higher.

SUMMARY OF THE INVENTION

The present invention provides a more efficient and economical route to production of vinyl acetate than previous processes. As stated above, the present process avoids many of the disadvantages in those previous processes. For example, the inventive process does not produce significant quantities of carbon dioxide and gives higher conversions per pass than the ethylene-based processes. In addition, the present invention avoids the large coproduction of acetic acid that plagues the synthesis gas-based processes. Moreover, the process does not require continuous introduction of acetic anhydride. Further advantages of the present invention are both set forth above and apparent from the examples set forth below.

The present invention relates to a process for the production of vinyl acetate comprising the steps of contacting a mixture of ketene and acetaldehyde with an acid catalyst in a contact zone and recovering vinyl acetate from the contact zone. More particularly, the present invention relates to a continuous process for the production of vinyl acetate comprising the steps of continuously feeding a gas comprising ketene and acetaldehyde and, optionally, a non-reactive diluent gas to a contact zone containing an acid catalyst and, optionally, a solvent; and continuously recovering a product comprising vinyl acetate from the contact zone. Our novel process for producing vinyl acetate has many advantages over the prior art processes, as set forth above, including more efficient production of vinyl acetate and improved yields.

DETAILED DESCRIPTION OF THE INVENTION

The object of the invention is to provide an efficient process for forming vinyl acetate by reacting acetaldehyde and ketene in the presence of an acid catalyst at about 85°–200° C. The ketene used can be produced by any of the common ketene-forming reactions such as acetic acid dehydration, acetic anhydride pyrolysis, diketene pyrolysis or acetone pryolysis. On an industrial scale, it is preferred to prepare the ketene from acetic acid pyrolysis for economic reasons. Similarly, acetaldehyde can be produced by any route, such as via the Wacker process or by ethanol dehydrogenation, provided that the acetaldehyde is free of large amounts of components that normally react with ketene. That is, it is preferable to have acetaldehyde that is substantially free of nucleophilic impurity components such as water or alcohols since these can react with ketene causing yield loss. It is often advantageous to include trace amounts (greater than about 5 ppm) of a polymerization inhibitor such as copper, or a hydroquinone derivative, in regions of the process where vinyl acetate is present, but this is not a requirement of the invention.

The process of the invention is performed within a contact zone where ketene, acetaldehyde and an acid catalyst are contacted. The contact zone can contain acid catalyst in a liquid solution, as a solid, or as a mixture of solid and liquid. The preferred acid should be a Bronsted acid. More preferred acids are those containing phosphorous or sulfur in a positive oxidation state, which includes the liquid phosphoric, sulfuric and methanesulfonic acids, the soluble solid benzene-sulfonic, p-toluenesulfonic, naphthalene-sulfonic and naphthalenedisulfonic acids and insoluble acidic ion exchange resins such as Amberlyst® 15 (a partially cross-linked sulfonic acid form of polystyrene) and Nafion® 117 (a perfluorinated sulfonic acid resin) polymeric sulfonic acids. Strong acids, such as sulfuric acid, cause excessive charring under the reaction conditions, and can produce byproduct acetic acid. Weak acids, such as methanesulfonic acid, give lower rates of reaction. Polystyrene-based catalysts, such as Amberlyst® 15, tend to slowly decompose under the reaction conditions. Volatile acids, such as methanesulfonic acid tend to leave the reaction zone with the product, which is undesirable. The still more preferred acids are arene sulfonic acids: benzene-sulfonic acid, p-toluenesulfonic acid, naphthalene sulfonic acids and naphthalenedisulfonic acids. In general p-toluenesulfonic acid is the most preferred acid because significant amounts of acetic acid are not produced after steady state operation is achieved.

When the contact zone contains acid catalyst in liquid solution, the acid concentration should range from about 0.005 to about 2.0 acid equivalents per liter of solution. The process of the invention is possible with acid concentrations outside this range, but excessively dilute acid concentrations tend to provide lower rates, and excessively high acid concentrations tend to cause excessive charring. The preferred acid concentrations depend on the acid used, the identity of the solvent, the contact time and the temperature. Thus, for example, when the acid is p-toluenesulfonic acid, the solvent is acetic anhydride, the space velocity is about 65 hr$^{-1}$ (units are liters of ketene+acetaldehyde at reaction temperature and pressure per liter of solution contacted per hour with the volume of any diluents excluded), and the temperature is 150° C., a more preferred acid concentration range is from about 0.01 to about 1.2 acid equivalents per liter of solution, and the most preferred acid concentration range is from about 0.03 to about 0.8 acid equivalents per liter of solution.

When the contact zone contains an insoluble solid acid, it should contain from about 0.01 to about 5 acid equivalents per liter of catalyst. Preferably the solid insoluble acid should contain from about 0.1 to about 3 acid equivalents per liter of catalyst and most preferably between 0.5 and 2 acid equivalents per liter of catalyst. After the solid insoluble acid is contacted with the ketene and acetaldehyde reactants under the reaction conditions, a liquid phase is formed, and the mode of operation will then change to that of a gas-liquid-solid mode.

When the contact zone contains acid catalyst in liquid solution, it is preferable that the acid, ketene and acetaldehyde have good solubility in the solvent. The solvent may or may not react with ketene or acetaldehyde to form reactive intermediates. Any interactions of the solvent with ketene or acetaldehyde should be such that any intermediate species formed are eventually converted to vinyl acetate. Ideally, the solvent should boil at a temperature equal to or greater than the temperature of the reaction. Examples of solvent classes suitable for reaction include, but are not limited to, polycyclic aromatic hydrocarbons such as naphthalene and their halogenated derivatives such as 1-chloronaphthalene, polar aprotic solvents such as N-methyl-2-pyrrolidinone, acetic anhydride, ethylidene diacetate and mixtures of these. By-product liquids from the reaction can be used as solvents or solvent components. The solvents may contain small amounts of water or acetic acid. The water and acetic acid will react with the ketene at the start of the reaction and will be converted largely to acetic anhydride. The preferred solvents for the reaction are acetic anhydride or acetic anhydride containing small amounts (about 10 mole % or less) of acetic acid. When these solvents are used with the preferred catalysts, EDA is produced at the beginning of the reaction and builds up to a constant level (about 20 to 40 weight % depending on the temperature), and the rate of the reaction increases as the level of EDA builds up and then stays relatively constant. However, when N-methyl-2-pyrrolidinone is used as a solvent, the level of EDA present in the solution stays at about one weight %. In general, when water is present in the solvent, or is associated with the acid catalyst, the efficiency of the reaction increases as the water is consumed.

Once the reaction rate has reached its maximum, the mass of the liquid solution contained in the contact zone remains essentially constant except for the slow formation of nonvolatile byproducts and any entrainment or volatilization of the solvent. Entrainment or volatilization of the solvent is minimized by the use of a distillation column to return these components to the contact zone solution while allowing vinyl acetate and any unreacted ketene or acetaldehyde to leave the contact zone. Slowly removing a portion of the liquid from the base of the contact zone and concurrently replenishing it with fresh liquid by means known to those skilled in the art may prevent excess nonvolatile byproduct accumulation.

The process of the invention can be performed at pressures ranging from about 0.05 to about 20 bars absolute. However, excessively high pressures increase the possibility of ketene polymerization reactions and, by decreasing product volatility, can make it more difficult to continuously recover the vinyl acetate product in those cases where the product must vaporize from a liquid medium. By contrast, excessively low pressures lower reaction rates, can complicate heat control and make it more difficult to condense and recover the vinyl acetate product. The process preferably is carried out at a pressure of from about 0.1 to about 5 bars with the most preferred range being from about 0.25 to about 2 bars. Further, because ketene is normally generated and used at a pressure of about one bar or less, the process of the invention is most conveniently carried out at a pressure of about one bar or less.

Diluent gas may be fed with the ketene and acetaldehyde, which can assist in removing the desired vinyl acetate product from the contact zone. However, excess amounts of diluent gas can increase the difficulty in condensing and recovering the vinyl acetate from the vapor phase. Diluent gases can comprise from about 0 to about 95 volume % of the ketene-acetaldehyde feed mixture. More preferred levels of diluent gases range from about 0 to about 90 volume %, and the most preferred levels of diluent gases range from about 0 to about 85 volume %. Diluent gases used should be those which do not react with the reactants or products under the reaction conditions. Suitable diluent gases include hydrocarbons such as methane, nitrogen, helium or other inert gas, hydrogen, and gases commonly present in ketene streams including, in addition to methane, carbon monoxide, propyne, allene, ethylene, acetylene and carbon dioxide. Air or other molecular oxygen-containing gases are not preferred diluent gases because of safety considerations, although the vinyl acetate producing reaction will occur if these gases are used as diluents.

The ratio of ketene to acetaldehyde is not critical and can range from about 0.1 to about 10. When a large excess of either reactant is used, the unreacted portion must either be recycled back to the reaction contact zone or otherwise used. If ketene is the reactant in excess, it can be recycled or converted to other useful products, such as acetic anhydride or diketene. If acetaldehyde is the reactant in excess, it can be recycled, recovered unchanged, or converted to other useful products such as pentaerythritol, synthetic pyridine derivatives or peracatic acid. A more preferred ratio of ketene to acetaldehyde is between about 0.2 and 5 and the most preferred ratio of ketene to acetaldehyde is between about 0.4 and 2.5.

The temperature of the contact zone may range from about 85° C. to about 200° C. Excessively low temperatures provide low rates and conversions whereas excessively high temperatures accelerate the rate of char formation, increase catalyst losses and provide little increase in rate. More preferred temperatures range from about 100° to about 180° C., and the most preferred temperature range is from about 120° to 160° C. when the contact zone contains acid catalyst in liquid solution. Amberlyst® insoluble solid acid catalysts decompose at elevated temperatures and should not be used at temperatures significantly above 120° C., but the Nafion® catalysts can be used at temperatures approaching 150° C.

The contact zone should be constructed to allow efficient contact with the acid catalyst, allow for sufficient time for the reactants to react, be able to receive nonvolatile components returned to the reactor and operate without significant heat or mass transfer limitations. The actual configuration of the contact zone can depend on the scale of the operation, flow rates, temperature, pressures, the level of diluent, the nature and amount of any solvents present and catalyst type and amount. In most cases the acetaldehyde and ketene are fed near the bottom of the contact zone along with any diluent gases. The simplest contact zone for an acid catalyst in a liquid solution is a cylindrical tube with provision for the gases to be sparged into the base of the tube.

In some instances, it may be preferable to circulate the liquid medium counter-current to the reactant gas streams to improve heat and mass transfer. The liquid containing the catalyst can be dispersed over a high surface area solid, if desired, to improve gas/liquid contact, but some degree of liquid circulation will be required to replenish the solid surface with fresh catalyst solution. The use of baffles, high speed stirrers or other gas dispersion devices to improve mass transfer is within the spirit of the invention.

If an insoluble solid acid catalyst is used, the reaction can be performed within the contact zone without the addition of any liquid. However, generally in this case, a liquid will eventually appear and will wet the catalyst. The insoluble solid acid can be supported in a tube and the reactants passed through the bottom of the tube or through the top of the tube, and generally the reactor will be operating in a trickle bed mode. Alternatively, the insoluble solid acid catalyst can be dispersed in a liquid and the reaction performed in a slurry mode contacting the reactants and suspensions in the same manner used for soluble catalysts and using the similar liquid components.

It is best to select the velocity of the reactants through the contact zone after other operating parameters are decided upon. This velocity can vary considerably depending on the other operating parameters, and must be adjusted experimentally to provide the optimum conversion of the limiting reagent and the highest selectivity and rate. Under operating conditions of 0.03 equivalents of arenesulfonic acid per mole of acetic anhydride solvent, at 130°–160° C., and with about 85% diluent gas present, between about 5 and 160 liters of acetaldehyde plus ketene vapor pass each liter catalyst solution per hour neglecting the volume of the diluent gas. More preferred feed rates under these conditions range between about 30 and 120 liters of acetaldehyde plus ketene vapor per liter of catalyst solution per hour neglecting the volume of the diluent gas. Most preferred feed rates under these conditions range between about 45 and 80 liters of acetaldehyde plus ketene vapor per liter of solution per hour neglecting the volume of the diluent gas.

The process of the invention can be operated as a continuous process as described above or, less preferably, as a batch process. A batch process may require, for example, that the desired quantities of reactants, solvents and catalysts be charged to a contact zone, heated under pressure until the reaction is completed, and then recovering the vinyl acetate by distillation. Batch operation is not preferred since prolonged heating of the reactants and products in the presence of the acid catalyst causes the formation of large amounts of byproducts. Thus, the process is preferably operated as a continuous process as described above. Owing to the short time that the reactants, products and acid catalysts are contacted at elevated temperature, the formation of undesirable byproducts is minimized when the process is operated in the continuous fashion described above. Once the continuous process reaches steady state performance, the rate of mass delivery to the contact zone approximately equals the rate of mass exit from the contact zone. Under the preferred operating conditions, acetic acid is not present in the product stream in significant quantities once steady state performance is reached.

The following examples are presented to illustrate the present invention, but are not intended in any way to limit the scope of the invention.

EXAMPLES

General Experimental Methods

An overview of the apparatus used in the examples follows, and the apparatus consisted of 7 major sections:

1. a gas delivery system,
2. a ketene generation section,
3. a ketene purification section,
4. a ketene trap/vaporizer section,
5. an acetaldehyde purification and delivery section, 6. a reactor-condenser train section,
7. a scrubber system.

These seven major sections were linked by a series of connecting lines and stopcocks. The gas delivery system provided four separate metered nitrogen flows to various points in the apparatus. The ketene generation section consisted of an acetic anhydride vaporizer/pyrolysis tube, chilled condenser and cyclone assembly. The ketene generation section produced raw ketene by acetic anhydride pyrolysis and accomplished the rapid separation of the ketene from the bulk of the coproduct acetic acid and unreacted acetic anhydride. The ketene purification section consisted of a demisting trap held at 0° C. (trap A) and a trap initially held at −78° C. (trap B) for the initial condensation and subsequent distillation of purified ketene to the ketene trap/vaporizer section. The ketene trap/vaporizer section served as a reservoir for purified ketene and also provided for metered delivery of ketene to the reactor. The ketene trap/vaporizer was held at −78° C. for the collection of the distilled ketene from trap B and its subsequent delivery to the reactor by transpiration in metered nitrogen. The acetaldehyde purification and delivery section consisted of a graduated cylinder from which acetaldehyde could be distilled and a trap/vaporizer held at −20° C. for the collection of the distilled acetaldehyde and subsequent delivery to the reactor by transpiration in metered nitrogen. The reactor-condenser train section consisted of a reactor where the ketene and acetaldehyde reacted, a water-cooled condenser to return condensable liquid to the reactor and an acetone/solid carbon dioxide condenser and trap (trap C) to collect the bulk of the vinyl acetate, vaporized acetic acid and unreacted acetaldehyde. The scrubber system contained a water scrubber for the destruction of ketene and an analytical scrubber containing acetic acid for the quantification of ketene and for the capture and quantification of any vinyl acetate or acetaldehyde not trapped by trap C of the reactor-condenser train section.

The apparatus was designed to allow the reactants to bypass the reactor as an option. The apparatus also had provision for a continuous flow of nitrogen to prevent back diffusion of scrubber fluids or contamination by air. Details of the construction of each section of the apparatus, how they are connected and the operation of the apparatus are described below.

In the gas delivery section, metered nitrogen gas flows were provided by four Tylan® Model FC-260 mass flow controllers. Metered nitrogen gases were fed through 4 gas lines L1 through L4, and each gas line was teed to a pressure relief column containing water to prevent accidental over pressurization. Two of these gas lines, L1 and L3, provided nitrogen purge to the apparatus. L1 provided nitrogen purge to the acetic anhydride pyrolysis unit, and L3 provided nitrogen purge to the rest of the apparatus at a point teed into the ketene trap/vaporizer outlet line described below. Gas lines L2 and L4 were used to meter ketene and acetaldehyde respectively from the ketene trap/vaporizer section and the acetaldehyde trap/vaporizer respectively by transpiration.

In the ketene generation section, ketene was generated by the method described by Fisher et al. in *J. Org. Chem.*, 18, 1055–1057 (1953) by the pyrolysis of acetic anhydride with minor modifications (Although acetic acid pyrolysis is the preferred industrial route to ketene, it is generally not practical on a laboratory scale). Acetic anhydride feed was provided by a Harvard Apparatus Model 22 syringe infusion pump. The acetic anhydride was fed to top of a 107 cm long by 25 mm O.D. vertical quartz vaporizer/pyrolysis tube along with nitrogen metered through line L1. Electric temperature control for the vaporizer/pyrolysis tube and monitoring were provided by a Dow Camile® control system interfaced with a Gateway Model 2000 486DX/33 computer. The vaporizer/pyrolysis tube was indented at a distance of 27 cm from the top and contained a 9 mm O.D. quartz thermocouple well extending about two thirds the length of the reactor from top towards the bottom. The portion of the vaporizer/pyrolysis tube extending 22 cm up from the indentations also contained quartz chips and was heated with heating tape controlled at 200° C. The lower section of the vaporizer/pyrolysis tube was heated by two heating tapes controlled at 520° C. The quenching condenser below the vaporizer/pyrolysis tube was held at about −55° C. by circulating methanol cooled in an acetone/solid carbon dioxide bath. The mixture from the quenching condenser passed sequentially through two identical cyclones measuring 16 mm O.D. at the top and 80 mm from the top of the cyclone body to the bottom of the tapered section. The inlet and outlet lines of the cyclone were 2 mm I.D., and the liquid from the bottom of the cyclone assembly was drained into a 1 liter bottle. The gas displacement tube (10 mm O.D.) connecting the drain flask to the cyclone assembly was bent to provide a liquid seal. The misted vapor from the ketene generator cyclone assembly was then passed to the ketene purification section.

In the ketene purification section, the ketene-containing vapor passed through a demisting trap held at 0° C. (trap A) to remove a portion of the entrained acetic anhydride-acetic acid. The ketene-containing stream exiting trap A then was sent to a trap held at −78° C. (trap B) where the ketene was condensed. The outlet line of trap B led to a three-way stopcock (SC1). In one position SC1 vented excess ketene-containing vapors from trap B to a line teed into the water scrubber. In another position SC1 sent the ketene-containing vapors to the ketene inlet line of a ketene trap/vaporizer assembly.

The ketene trap/vaporizer assembly was a modified two-piece 32×200 mm vacuum trap having the bottom portion of the trap narrowed to 19 mm O.D. and extending an additional 100 mm. A 7 mm O.D./2 mm I.D. gas inlet tube extended along the outer body of the ketene trap/vaporizer assembly and was connected to the base of the extended tube section. The gas inlet tube was connected to the metered nitrogen line L2 containing a stopcock (SC2). The purpose of SC2 was to prevent diffusion of ketene into line L2 when no nitrogen was flowing through it during the ketene generation process and when the ketene trap/vaporizer was being loaded. The ketene inlet line was the normal inside 10 mm O.D. tube found in the standard vacuum trap design. The ketene trap/vaporizer outlet line was the normal 10 mm O.D. side tube found in the standard vacuum trap design. The ketene trap/vaporizer outlet line was teed into the nitrogen purge line L3. After the teeing to purge line L3, the ketene trap vaporizer line connected to a three-way stopcock SC3. Further connections to SC3 are described later below.

The acetaldehyde purification and delivery section contained an acetaldehyde trap/vaporizer of identical construction to the ketene trap/vaporizer except that it was surrounded by a jacket for liquid coolant which was in turn enclosed by a vacuum jacket. Line L4 provided metered nitrogen to the acetaldehyde trap/vaporizer gas inlet tube. The acetaldehyde trap/vaporizer inlet line allowed for the introduction of acetaldehyde distilled from a graduated cylinder. The acetaldehyde trap/vaporizer outlet line was connected to three-way stopcock SC4. Further connections to SC4 are described later below.

The reactor-condenser train contained a reactor, a reflux condenser and an acetone/solid carbon dioxide condenser. Details of the reactor design are provided in the individual examples. Reactants entered the reactor via line L6. The top of each reactor was fitted to the water-cooled reflux condenser to provide for the return of condensable liquids to the reactor. The top of the reflux condenser was attached to an acetone/solid carbon dioxide condenser. Material condensing in the acetone/solid carbon dioxide condenser was not returned to the reactor but collected in a trap flask (trap C) fitted to the base of the condenser. Trap C contained tert-butylhydroquinone (TBHQ, about 40 polymerization inhibitor, and trap C was also kept chilled with solid carbon dioxide. The majority of the vinyl acetate was found in trap C along with most of the unreacted acetaldehyde. Any acetic acid vaporizing from the reactor was found in trap C. The outlet of the acetone/solid carbon dioxide condenser was attached to the reactor-condenser train outlet line L7.

The scrubber system contained a water scrubber for the destruction of ketene and an analytical scrubber containing acetic acid for the quantification of ketene (as acetic anhydride) and for the capture and quantification of any vinyl acetate or acetaldehyde not trapped by trap C of the reactor-condenser train section. The acetic acid (about 60 Ml) in the analytical scrubber also contained TBHQ (about 40 polymerization inhibitor. The analytical scrubber fluid was circulated by a Masterflex® peristaltic pump. A stopcock at the base of the analytical scrubber provided for removal of the scrubber fluid for analysis, and a Claisen adapter at the top of the analytical scrubber allowed for the addition of fresh scrubber fluid. An acetone/solid carbon dioxide condenser was attached to the top of the vertical arm of the Claisen adapter to prevent loss of scrubber fluids. Access to the scrubber system was provided by three-way stopcock SC5. In one position, SC5 sent vapor streams to the water scrubber, and, in another position, SC5 sent vapor streams to the analytical scrubber.

The seven major sections were connected by a series of connecting lines, tees and stopcocks. The three-way stopcock SC3 connected the ketene trap/vaporizer outlet line at the point past the L3 purge tee to the three-way stopcock SC4 via line L5 or to the reactor bypass line. Three-way stopcock SC4 connected line L5 to the acetaldehyde trap/vaporizer outlet line and to the reactor-condenser train inlet line L6. The bypass line attached to SC3 was teed to the reactor-condenser train outlet line L7 and the other arm of the tee was connected to SC5. SC5 directed the gas stream from the reactor-condenser train outlet line L7 or from the bypass line to the water scrubber or to the analytical scrubber as stated above. A description of the operation of the apparatus follows.

Acetic anhydride (600 Ml/minute) and nitrogen (25 standard cubic centimeters per minute, SCCM) through L1 were fed to the ketene generation section for 20 minutes, and the product was condensed in trap B held at −78° C. by an acetone/solid carbon dioxide bath in the ketene purification section. During the ketene generation/condensation process, vented gases leaving trap B were allowed to pass through SC1 to the ketene trap/vaporizer and then to the water scrubber via stopcock SC3, the bypass line and SC5. Stopcock SC2 was closed during the ketene generation process, and the ketene trap/vaporizer was kept at −78° C. During the ketene generation process, ketene purification process and at all other times that reactants were not flowing to the reactor, a nitrogen purge (25 SCCM) was flowing through line L3. The −78° C. bath was then removed from trap B and the liquid ketene was then allowed to evaporate and condense in the ketene trap/vaporizer. The evaporation process, which took about an hour, provided about 30 Ml pure liquid ketene condensate in the ketene trap/vaporizer. Stopcock SC1 was then turned to disengage the ketene trap/vaporizer from the ketene generation and purification sections and allowed any vapors leaving the ketene generation and purification sections to access the water scrubber.

The acetaldehyde trap/vaporizer was loaded by charging reagent grade acetaldehyde to a graduated cylinder and then distilling the acetaldehyde with a warm water bath into the acetaldehyde trap/vaporizer held at −20° C. During the acetaldehyde loading procedure, no gas was flowing through L4 and the acetaldehyde trap/vaporizer outlet line was accessed to the water scrubber through SC4, SC3 and SC5 with nitrogen (25 SCCM) flowing through L3.

The reactant metering was begun by opening SC2 and feeding nitrogen (88 SCCM) to the ketene trap/vaporizer gas inlet tube through line L2 while maintaining the ketene trap/vaporizer at −78° C. These conditions provided 0.7 mmol ketene/minute. Nitrogen (118 SCCM) was fed to the acetaldehyde trap/vaporizer gas inlet tube through line L4 while maintaining the acetaldehyde trap/vaporizer at −20° C. These conditions provided 1.0 mmol acetaldehyde/minute. Stopcocks SC3 and SC4 were positioned with all three ports of each stopcock opened, and SC5 was positioned to provide venting to the water scrubber. With the stopcocks positioned in this manner, the reactants and diluent gases flowed through the bypass line, and no flow to the reactor occurred because the pressure drop across the reactor was greater than the pressure drop across the bypass line. The purge nitrogen to line L3 was then shut off, and access to the bypass line was blocked by turning SC3 to send the nitrogen/ketene stream to SC4 via line L5 where it mixed with the nitrogen/acetaldehyde stream and proceeded to the reactor-condenser train via line L6. At this time stopcock SC5 was positioned to send the vapors exiting the reactor-condenser train to the acetic acid analytical scrubber. The reactor heater was also turned on at this time. Reactions were normally conducted for several hours each day, and the time required to heat the reactor (about 20 minutes) was normally small compared to the total time that the reactor was heated. The reaction was terminated by opening SC3 to access all streams to the bypass line, switching SC5 to the water scrubber, terminating nitrogen flow to L2 and L4, closing SC2, resuming purge nitrogen to L3, and discontinuing the heat to the reactor. The condensed liquid in trap C of the reactor-condenser train was removed, weighed and analyzed. The acetic acid analytical scrubber was allowed to warm up overnight, and the scrubber solution then drained, weighed and analyzed. Normally reactions were performed for several days in this manner before changing the catalyst charge. When the catalyst solution (the reactor heel) was removed from the liquid phase reactor, it was weighed and analyzed. When the catalyst was removed from the reactor containing an insoluble solid catalyst, the liquid remaining at the base of the reactor (the reactor heel) was weighed and analyzed.

Products obtained from the trap C of the reactor-condenser train, acetic acid scrubber solution and reactor heel were analyzed by gas chromatography using Hewlett Packard Model 5890 gas chromatographs using flame ionization detectors. Vinyl acetate, acetaldehyde and acetic acid were analyzed using a 25 m×0.53 mm FFAP capillary column (1.0 micron film thickness) programmed at 40° C. for 5 minutes, 15° C./minute to 235° C. and holding at 235° C. for 1.67 minutes. Acetic anhydride and ethylidene diacetate were analyzed using a 30 m×0.53 mm DB-5 capillary column (1.5 micron film thickness) programmed at 40° C. for 8 minutes, 7° C./minute to 200° C. with a 0 minute holding time at 200° C. Mixtures were prepared for gas chromatographic analysis by adding 5 Ml of a tetrahydrofuran solution containing 2 % decane internal standard to an accurately weighed 1 g sample of the reaction product.

In the examples that follow, the percent yield vinyl acetate is defined as 100 times the moles of vinyl acetate produced divided by the moles of ketene fed.

Example 1

This example illustrates the process of the invention performed with the reactor zone containing acetic anhydride solvent and p-toluenesulfonic acid catalyst at 150° C. and a pressure of about 1 bar absolute. The example also illustrates conditions that provide high yields of vinyl acetate without the production of acetic acid after a steady state has been reached (Examples 1.2 through 1.4). The reactor was a 36 mm O.D. X 175 mm long tube sealed on one end. The reactor was mounted vertically with the open end facing upward. The reactor was loaded with acetic anhydride (65.8 g, 0.645 mol), p-toluenesulfonic acid monohydrate (5.8 g, 0.0306 mol) and TBHQ (140 mg, 0.84 mmol) polymerization inhibitor. The reactor tube was placed in a temperature-controlled electric heater. A three-way claisen adapter was attached to the open end of the reactor. A 10 mm O.D. gas delivery tube with the bottom end drawn down to 1 mm I.D. was inserted through the straight vertical arm of the claisen adapter and extended to within about 1 mm of the base of the reactor. A threaded connector bushing at the top of the vertical arm of the claisen adapter held the gas delivery tube in place and provided a seal. The reactor inlet line L6 was connected to the gas delivery tube. The curved side arm of the claisen adapter was attached to the base of the reflux condenser portion of the condenser train assembly. To begin the reaction of Example number 1.1, stopcock SC3 was positioned to block access to the bypass line thus sending ketene (0.7 mmol/minute), acetaldehyde (1.0 mmol/minute) and nitrogen (206 SCCM) to the reactor through the gas delivery tube with the gas exiting the reactor contacting the water-chilled reflux condenser, solid carbon dioxide/acetone cooled condenser and trap flask (trap C) containing TBHQ (40 mg, 0.24 mmol), and SC5 was positioned to send the product exiting the solid carbon dioxide/acetone condenser to the acetic acid (also containing about 40 mg TBHQ) scrubber, and the heater temperature was set for 150° C. The 150° C. reactor temperature was reached after 20 minutes. The reaction was allowed to continue in this manner for a total of 314 minutes. To terminate the reaction, SC3 was positioned to divert the reactant gases through the reactor bypass line, the heating of the reactor was discontinued, and SC5 was positioned to send all gases to the water scrubber. The gas feeds were shut off, and the reactor system was accessed to nitrogen (25 SCCM) flowing through line L3 during the cooling period and at all other times it was idle. The liquid contained in trap C was weighed and analyzed by gas chromatography. The acetic acid scrubber was allowed to warm to room temperature and drain overnight. The product recovered from the acetic acid scrubber was weighed and analyzed by gas chromatography. The reactor heel solution was retained in the reactor. Example numbers 1.2, 1.3 and 1.4 were performed by conducting the reaction in the manner of example number 1.1 for time periods of 301, 300 and 300 minutes respectively using the same reactor heel solution. Yields of vinyl acetate isolated from the condenser train trap C and the acetic acid scrubber solutions and the wt % acetic acid contained in trap C (trap C wt % HOAc) follow.

| Example Number | % Yield Vinyl Acetate | Trap C Wt % HOAc |
|---|---|---|
| 1.1 | 42 | 1.13 |
| 1.2 | 78 | 0 |
| 1.3 | 78 | 0 |
| 1.4 | 81 | 0 |

The reactor heel solution remaining from Example 1.4 was weighed and analyzed by gas chromatography. The recovered heel solution (86.73 g) contained acetaldehyde (0.31 wt %), vinyl acetate (1.7 wt %), acetic acid (1.14 wt %), acetic anhydride (57.32 wt %) and EDA (28.99 wt %).

Example 2

This example illustrates the effect of operating the process of Example 1 at a lower temperature. The example also illustrates conditions that provide high yields of vinyl acetate without the production of acetic acid after a steady state has been reached (Examples 2.2 through 2.5). The same reactor system used in Example 1 was used in Example 2. The reactor tube was loaded with acetic anhydride (65.8 g, 0.645 mol), p-toluenesulfonic acid monohydrate (5.8 g, 0.0306 mol) and TBHQ (140 mg, 0.84 mmol) polymerization inhibitor as per Example 1. The reactor was operated in the same manner as per Example 1 except that the temperature was set for 140° C. Example numbers 2.1, 2.2, 2.3, 2.4 and 2.5 were each conducted for 300 minutes using the same heel solution. Yields of vinyl acetate isolated from trap C and the acetic acid scrubber solutions and the wt % acetic acid contained in trap C (trap C wt % HOAc) follow.

| Example Number | % Yield Vinyl Acetate | Trap C Wt % HOAc |
|---|---|---|
| 2.1 | 37 | 2.81 |
| 2.2 | 75 | 0 |
| 2.3 | 74 | 0 |
| 2.4 | 75 | 0 |
| 2.5 | 80 | 0 |

The reactor heel solution recovered from Example 2.5 was analyzed by gas chromatography. The recovered heel solution (88.18 g) contained acetaldehyde (0.41 wt %), vinyl acetate (1.59 wt %), acetic acid (1.03 wt %), acetic anhydride (47.65 wt %) and EDA (39.42 wt %).

Example 3

This example illustrates the effect of operating the process of Example 1 at a higher temperature. The example also illustrates conditions that provide high yields of vinyl acetate without the production of acetic acid after a steady state has been reached (Examples 3.2 through 3.5). The same reactor system used in Example 1 was used in Example 3. The reactor tube was loaded with acetic anhydride (65.8 g, 0.645 mol), p-toluenesulfonic acid monohydrate (5.8 g, 0.0306 mol) and TBHQ (140 0.84 mmol) polymerization inhibitor as per Example 1. The reactor was operated in the same manner as per Example 1 except that the temperature was set for 160° C. Example numbers 3.1, 3.2, 3.3, 3.4 and 3.5 were each conducted for 300 minutes using the same heel solution. Yields of vinyl acetate isolated from trap C and the acetic acid scrubber solutions and the wt % acetic acid contained in trap C (trap C wt % HOAc) follow.

| Example Number | % Yield Vinyl Acetate | Trap C Wt % HOAc |
| --- | --- | --- |
| 3.1 | 45 | 2.94 |
| 3.2 | 76 | 0 |
| 3.3 | 82 | 0 |
| 3.4 | 82 | 0 |
| 3.5 | 82 | 0 |

The reactor heel solution recovered from Example 3.5 was analyzed by gas chromatography. The recovered heel solution (86.31 g) contained acetaldehyde (0.33 wt %), vinyl acetate (1.41 wt %), acetic acid (1.23 wt %), acetic anhydride (56.12 wt %) and EDA (28.82 wt %).

Example 4

This example illustrates the process of the invention performed with the reactor zone containing N-methyl-2-pyrrolidinone solvent and p-toluenesulfonic acid catalyst at 150° C. and at a pressure of about 1 bar absolute. The example also illustrates conditions that provide high yields of vinyl acetate without the production of acetic acid after a steady state has been reached (Examples 4.2 through 4.5). The same reactor system used in Example 1 was used in Example 4. The reactor tube was loaded with N-methyl-2-pyrrolidinone (63.2 g, 0.638 mol), p-toluenesulfonic acid monohydrate (5.8 g, 0.0306 mol) and TBHQ (140 mg, 0.84 mmol) polymerization inhibitor. The reactor was operated in the same manner as per Example 1 at 150° C. Example numbers 4.1, 4.2, 4.3, 4.4 and 4.5 were conducted for 300, 330, 300, 305 and 300 minutes respectively using the same heel solution. Yields of vinyl acetate isolated from trap C and the acetic acid scrubber solutions and the wt % acetic acid contained in trap C (trap C wt % HOAc) follow.

| Example Number | % Yield Vinyl Acetate | Trap C Wt % HOAc |
| --- | --- | --- |
| 4.1 | 59 | 0.8 |
| 4.2 | 76 | 0 |
| 4.3 | 77 | 0 |
| 4.4 | 71 | 0 |
| 4.5 | 68 | 0 |

The reactor heel solution recovered from Example 4.5 was analyzed by gas chromatography. The recovered heel solution (80.81 g) contained vinyl acetate (1.04 wt %), acetic acid (1.01 wt %), acetic anhydride (4.73 wt %) and a small amount of EDA (1.13 wt %).

Example 5

This example illustrates the process of the invention performed with the reactor zone containing mixed acetic anhydride-acetic acid solvent and p-toluenesulfonic acid catalyst at 150° C. and at a pressure of about 1 bar absolute. The example also illustrates conditions that provide high yields of vinyl acetate without the production of acetic acid after a steady state has been reached (Examples 5.2 through 5.4). The same reactor system used in Example 1 was used in Example 5. The reactor tube was loaded with acetic anhydride (59.5 g, 0.583 mol), acetic acid (3.7 g, 0.0616 mol) p-toluenesulfonic acid monohydrate (5.8 g, 0.0306 mol) and TBHQ (140 mg, 0.84 mmol) polymerization inhibitor. The reactor was operated in the same manner as per Example 1 at 150° C. Example numbers 5.1, 5.2, 5.3 and 5.4 were conducted for 340, 300, 300 and 300 minutes respectively using the same heel solution. Yields of vinyl acetate isolated from trap C and the acetic acid scrubber solutions and the wt % acetic acid contained in trap C (trap C wt % HOAc) follow.

| Example Number | % Yield Vinyl Acetate | Trap C Wt % HOAc |
| --- | --- | --- |
| 5.1 | 41 | 16.2 |
| 5.2 | 86 | 0 |
| 5.3 | 95 | 0 |
| 5.4 | 87 | 0 |

The reactor heel solution recovered from Example 5.4 was analyzed by gas chromatography. The recovered heel solution (80.68 g) contained acetaldehyde (0.36 wt %), vinyl acetate (0.71 wt %), acetic anhydride (62.53 wt %) and EDA (35.7 wt %).

Example 6

This example illustrates the process of the invention performed with the reactor zone containing mixed acetic anhydride-acetic acid solvent and at 150° C. as per Example 5 but with benzenesulfonic acid catalyst instead. The example also shows that the stronger acid catalyst continues to produce acetic acid after the vinyl acetate yield has maximized (Examples 6.2 through 6.4). The same reactor system used in Example 1 was used in Example 6. The reactor tube was loaded with acetic anhydride (59.5 g, 0.583 mol), acetic acid (3.7 g, 0.0616 mol), benzenesulfonic acid monohydrate (5.4 g, 0.0306 mol) and TBHQ (140 mg, 0.84 mmol) polymerization inhibitor. The reactor was operated in the same manner as per Example 1 at 150° C. Example numbers 6.1, 6.2, 6.3 and 6.4 were conducted for 305, 300, 300 and 300 minutes respectively using the same heel solution. Yields of vinyl acetate isolated from trap C and the acetic acid scrubber solutions and the wt % acetic acid contained in trap C (trap C wt % HOAc) follow.

| Example Number | % Yield Vinyl Acetate | Trap C Wt % HOAc |
| --- | --- | --- |
| 6.1 | 50 | 10.25 |
| 6.2 | 90 | 2.56 |
| 6.3 | 92 | 2.52 |
| 6.4 | 78 | 3.54 |

The reactor heel solution recovered from Example 6.4 was analyzed by gas chromatography. The recovered heel solution (83.24 g) contained vinyl acetate (0.55 wt %), acetic acid (3.18 wt %), acetic anhydride (58.7 wt %) and EDA (33.07 wt %).

Example 7

This example illustrates the process of the invention performed with the reactor zone containing mixed acetic anhydride-acetic acid solvent and at 150° C. as per Example 6 but with methanesulfonic acid catalyst instead. The example also illustrates that acetic acid is not produced when a weaker acid is used but that the vinyl acetate yield is lowered. The same reactor system used in Example 1 was used in Example 7. The reactor tube was loaded with acetic anhydride (59.5 g, 0.583 mol), acetic acid (3.7 g, 0.0616 mol), methanesulfonic acid (2.9 g, 0.0306 mol) and TBHQ (140 mg, 0.84 mmol) polymerization inhibitor. The reactor was operated in the same manner as per Example 1 at 150° C. Example numbers 7.1, 7.2 and 7.3 were conducted for 300, 300 and 305 minutes respectively using the same heel solution. Yields of vinyl acetate isolated from trap C and the acetic acid scrubber solutions and the wt % acetic acid contained in trap C (trap C wt % HOAc) follow.

| Example Number | % Yield Vinyl Acetate | Trap C Wt % HOAc |
|---|---|---|
| 7.1 | 23 | 0 |
| 7.2 | 32 | 0 |
| 7.3 | 26 | 0 |

The reactor heel solution recovered from Example 7.3 was analyzed by gas chromatography. The recovered heel solution (75.31 g) contained vinyl acetate (0.91 wt %), acetic acid (1.22 wt %), acetic anhydride (79.9 wt %) and EDA (9.69 wt %).

Example 8

This example illustrates the process of the invention performed with the reactor zone containing mixed acetic anhydride-acetic acid solvent and at 150° C. as per Example 7 but with sulfuric acid catalyst instead. The example also illustrates that strong acids lower the vinyl acetate yield and produce acetic acid. The same reactor system used in Example 1 was used in Example 8. The reactor tube was loaded with acetic anhydride (59.5 g, 0.583 mol), acetic acid (3.7 g, 0.0616 mol), 96.8% sulfuric acid (3.1 g, 0.0306 mol) and TBHQ (140 mg, 0.84 mmol) polymerization inhibitor. The reactor was operated in the same manner as per Example 1 with the temperature set for 150° C. for 300 minutes. The yield of vinyl acetate isolated from trap C and the acetic acid scrubber was 12%, and trap C contained 19.28 wt. % acetic acid. Plugging of the gas delivery tube due to excessive char formation prevented further operation of the reactor containing this heel solution. The liquid portion (58.28 g) of the heel mixture was recovered, and it contained acetic acid (21.14 wt. %), acetic anhydride (55.83 wt. %) and EDA (24.95 wt. %).

Example 9

This example illustrates the process of the invention performed with the reactor zone containing mixed acetic anhydride-acetic acid solvent and at 150° C. as per Example 8 but with phosphoric acid catalyst instead. The example also illustrates that strong acids lower the vinyl acetate yield and produce acetic acid. The same reactor system used in Example 1 was used in Example 9. The reactor tube was loaded with acetic anhydride (59.5 g, 0.583 mol), acetic acid (3.7 g, 0.0616 mol), 85% phosphoric acid (3.53 g, 0.0306 mol) and TBHQ (140 mg, 0.84 mmol) polymerization inhibitor. The reactor was operated in the same manner as per Example 1 with the temperature set for 150° C. for 300 minutes. The yield of vinyl acetate isolated from trap C and the acetic acid scrubber was 19%, and trap C contained 13.84 wt. % acetic acid. Plugging of the gas delivery tube due to excessive char formation allowed for further operation of the reactor containing this heel solution for only 65 minutes. The liquid portion (72.25 g) of the heel mixture was recovered, and it contained vinyl acetate (0.84 wt. %), acetic acid (1.98 wt. %), acetic anhydride (77.55 wt. %) and EDA (32.78 wt. %).

Example 10

This example illustrates the process of the invention with the reactor zone containing the insoluble solid acid catalyst Amberlyst® 15 and no added solvent. The glass reactor used in this example consisted of a 74 cm by 25 mm O.D. tube fitted with a permanent thermowell extending from the base of the reactor. The central portion of the reactor tube was constructed with a condenser jacket which was in turn enclosed with a vacuum jacket to prevent heat loss. The length of the jacketed portion was 61 cm. The 25 mm O.D. tube had indentations 5 cm above the base of the jacket to support the catalyst bed. A physical mixture of Amberlyst® 15 resin (17 M1, 10.26 g, ca. 31 meq —$SO_3H$) and 16×24 mesh quartz chips (50 M1) was prepared. The base of the reactor was loaded with 6×6 mm Raschig rings to a height of 6 cm above the indentations, and a 1 cm high layer of 4×8 mesh quartz chips was placed on top of the Raschig rings. The entire mixture of Amberlyst® 15 and 16×24 mesh quartz chips was then placed in the reactor. The length of the catalyst+quartz mixture charge was 20 cm. An additional 5 cm high layer of 4×8 mesh quartz chips was placed on top of the catalyst bed. A 100 M12-necked flask was attached to the bottom of the reactor. The reactor inlet line L6 was attached to the other neck of the 100 M12-necked flask. The bottom of the reflux condenser portion condenser train was attached to the top of the reactor to allow for the return of condensable liquids to the reactor. The 100 M12-necked flask served as a heel reservoir for any liquid draining from the reactor. Under the conditions of the example, liquid did not flow into the heel reservoir until after the reaction feed flows to the reactor were terminated. Ketene, acetaldehyde and nitrogen were delivered to the reactor at a pressure of about 1 bar absolute at the same rate as per Example 1 to begin Example 10.1. The temperature of the catalyst bed slowly rose from 19.6° C. to 83.3° C. after which steam was delivered to the reactor condenser jacket. The catalyst bed temperature continued to slowly rise to 110.6° C. and then slowly decreased and leveled out at 98.7° C. During the process of Example 10.1, the catalyst bed slowly wetted. The reaction was terminated as per example 1 after 360 minutes after which a portion of the liquid wetting the catalyst bed drained into the reservoir. In Examples 10.2 through 10.5, the reactor was operated in the same fashion as per Example 10.1 except that steam heating of the reactor was commenced when the feeds were initially delivered to the reactor. Examples 10.2, 10.3, 10.4 and 10.5 were performed over periods of 300, 330, 300 and 352 minutes respectively using the same catalyst bed. Yields of vinyl acetate isolated from trap C and the acetic acid scrubber solutions and the wt % acetic acid contained in trap C (trap C wt % HOAc) follow.

| Example Number | % Yield Vinyl Acetate | Trap C Wt % HOAc |
|---|---|---|
| 10.1 | 10 | 14.44 |
| 10.2 | 44 | 0 |
| 10.3 | 37 | 1.97 |
| 10.4 | 34 | 0 |
| 10.5 | 31 | 0 |

The reactor heel solution recovered from reservoir after the completion of the reaction of Example 10.5 was analyzed by gas chromatography. The recovered heel solution (8.1 g) contained acetaldehyde (3.46 wt %), acetic acid (1.17 wt %), acetic anhydride (2.01 wt %) and EDA ( 39.9 wt % ).

We claim:

1. A process for preparing vinyl acetate comprising the steps of 1) contacting, at a temperature of about 85° to about 200° C. and at a pressure of about 0.05 to about 20 bars absolute, a mixture of ketene and acetaldehyde with an acid catalyst in a contact zone and 2) recovering vinyl acetate from the contact zone.

2. The process of claim 1 wherein the contacting is carried out at about 100° to about 180° C. and at about 0.1 to about 5 bars absolute.

3. The process of claim 2 wherein the contacting is carried out at about 120° to about 160° C. and at about 0.25 to about 2 bars absolute.

4. The process of claim 3 wherein the contacting is carried out at about 0.25 to about 1 bar absolute.

5. The process of claim 1 wherein a nonreactive diluent gas is fed into the contact zone with the mixture of ketene and acetaldehyde.

6. The process of claim 1 wherein the acid catalyst comprises a Bronsted acid.

7. The process of claim 6 wherein the contact zone further contains a solvent.

8. A process for preparing vinyl acetate comprising the steps of 1) contacting, at a temperature of about 85° to 200° C. and at a pressure of about 0.05 to about 20 bars absolute, a mixture of ketene and acetaldehyde and, optionally, a non-reactive diluent gas with an acid catalyst comprising a Bronsted acid and, optionally, a solvent in a contact zone; and 2) recovering vinyl acetate from the contact zone.

9. A process as set forth in claim 8 wherein the contacting is at a temperature of about 100° to about 180° C. and a pressure of about 0.1 to about 5 bars absolute.

10. A process as set forth in claim 9 wherein the contacting is at a temperature of about 120° to about 160° C. and a pressure of about 0.25 to about 2 bars absolute.

11. A continuous process for the production of vinyl acetate comprising the steps of 1) continuously feeding a gas containing ketene, acetaldehyde and, optionally, a non-reactive diluent gas to a contact zone, at a temperature of about 85° to about 200° C. and at a pressure of about 0.05 to about 20 bars absolute, containing an acid catalyst comprising a Bronsted acid and, optionally, a solvent; and 2) continuously recovering a product containing vinyl acetate from the contact zone.

12. A continuous process according to claim 11 wherein the contact zone is at a temperature of about 100° to about 180° C. and at a pressure of about 0.1 to about 5 bars absolute.

13. A continuous process according to claim 12 wherein the contact zone is at a temperature of about 120° to about 160° C. and at a pressure of about 0.25 to about 2 bars absolute.

14. A continuous process for preparing vinyl acetate comprising the steps of 1) continuously feeding a gas containing ketene, acetaldehyde and a non-reactive diluent gas to a contact zone, at a temperature of about 85° to about 200° C. and at a pressure of about 0.05 to about 20 bars absolute, containing an acid catalyst comprising a Bronsted acid and a solvent; and 2) continuously recovering a product containing vinyl acetate from the reaction zone.

15. A continuous process according to claim 14 wherein the contact zone is at a temperature of about 100° to about 180° C. and at a pressure of about 0.1 to about 5 bars absolute.

16. A continuous process according to claim 15 wherein the contact zone is at a temperature of about 120° to about 160° C. and at a pressure of about 0.25 to about 2 bars absolute.

17. A continuous process according to claim 14 wherein the product recovered from the contact zone is a gas.

18. A continuous process according to claim 14 wherein the Bronsted acid is selected from the group consisting of phosphoric acid, sulfuric acid, methanesulfonic acid, benzenesulfonic acid, p-toluenesulfonic acid, naphthalenesulfonic acid, naphthalenedisulfonic acid, and an acidic ion exchange resin.

19. A continuous process according to claim 18 wherein the Bronsted acid is p-toluenesulfonic acid.

* * * * *